Figure 1:
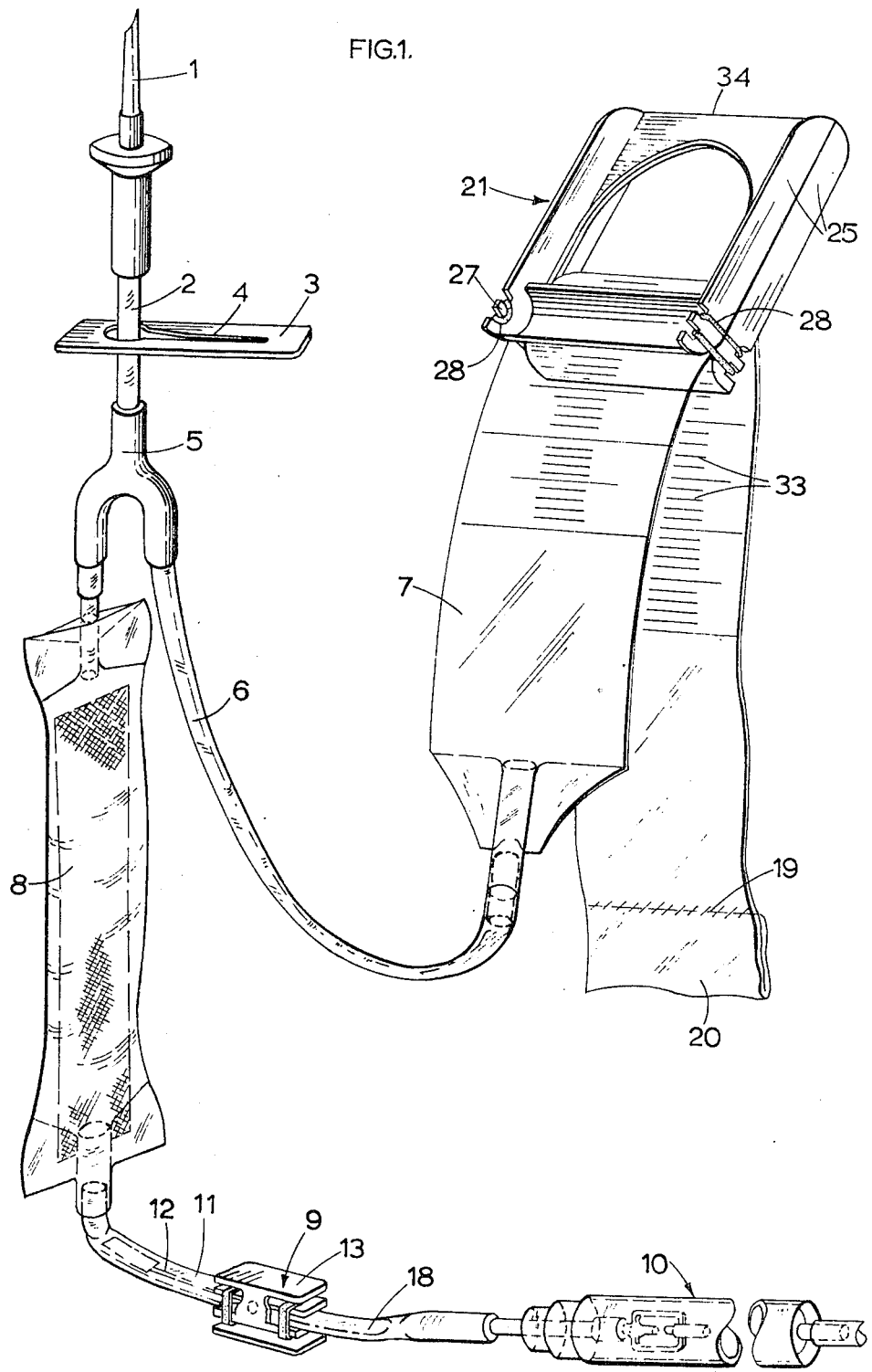

United States Patent [19]
Clarke

[11] 3,949,744
[45] Apr. 13, 1976

[54] APPARATUS FOR THE ADMINISTRATION OF LIQUIDS

[76] Inventor: Ellis Whiteside Clarke, 47 Deramore Drive, Belfast, Ireland, NS9 5JS

[22] Filed: Sept. 3, 1974

[21] Appl. No.: 502,680

[30] Foreign Application Priority Data
Sept. 4, 1973 United Kingdom............... 41634/73

[52] U.S. Cl....... 128/214 R; 128/214 D; 128/214.2; 222/95; 222/103
[51] Int. Cl.²......................................... A61M 5/14
[58] Field of Search........ 128/214, 214.2, 213, 227, 128/DIG. 24; 222/95, 103, 407

[56] References Cited
UNITED STATES PATENTS

| | | | |
|---|---|---|---|
| 2,682,354 | 6/1954 | Sam...................................... | 222/95 |
| 2,969,063 | 1/1961 | Broman............................ | 128/214.2 |
| 3,100,486 | 8/1963 | Nehring............................ | 128/214 R |
| 3,194,452 | 7/1965 | Sanderford......................... | 222/407 |
| 3,467,095 | 9/1969 | Ross................................. | 128/214.2 |
| 3,777,697 | 12/1973 | Woessner......................... | 128/227 X |
| 3,784,323 | 1/1974 | Sausse.......................... | 128/214 R X |
| 3,810,461 | 5/1974 | McCormick.................... | 222/103 X |

*Primary Examiner*—Dalton L. Truluck
*Attorney, Agent, or Firm*—Scrivener Parker Scrivener and Clarke

[57] ABSTRACT

Apparatus for administering liquids such as blood or saline solution comprises a readily collapsible but substantially inextensible container with a duct through which liquid can leave the container. Take-up means is provided to restrict the volume of that part of the container communicating with the duct, and referred to as the operative part. The take-up means is adjustable to vary the volume of the operative part. Calibration means is provided to enable the volume or the changes in volume of the operative part to be measured. In one type of construction the duct leads to a junction between a liquid inlet which may be connected to a source of liquid, and a liquid outlet, such as a terminal connector connectable to a needle, a catheter or the like.

12 Claims, 6 Drawing Figures

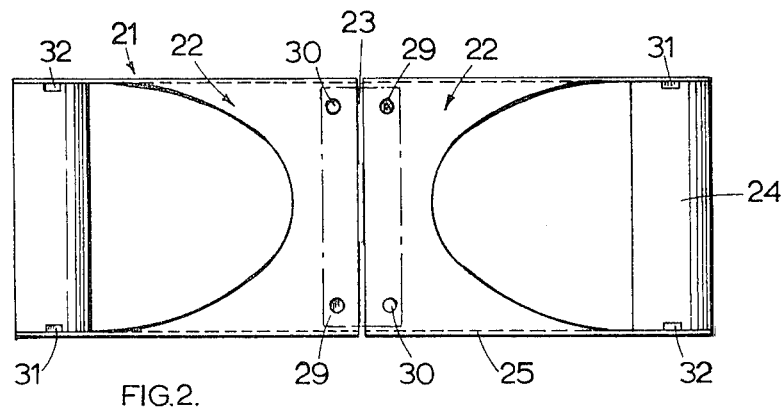
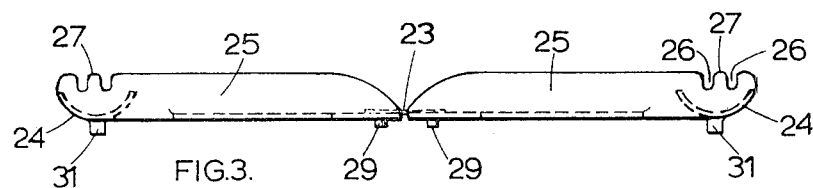
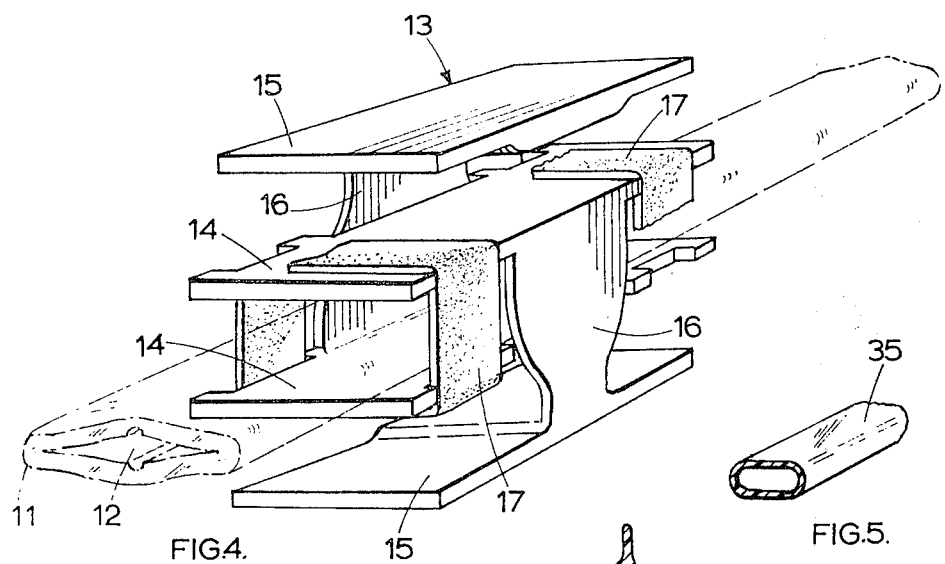
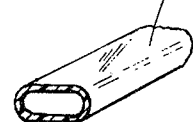
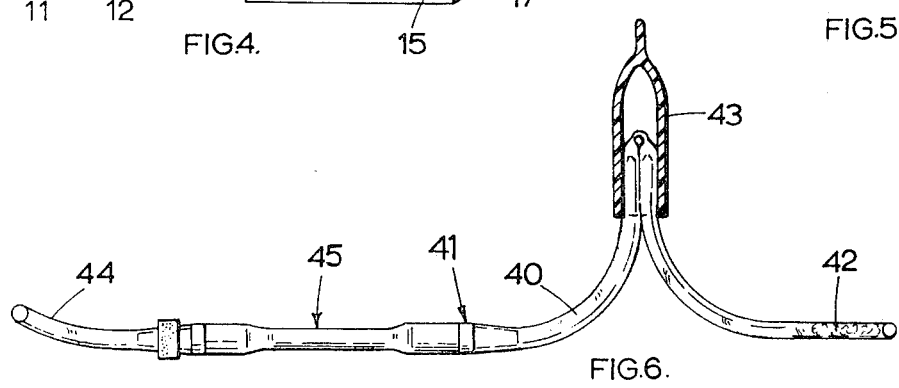

APPARATUS FOR THE ADMINISTRATION OF LIQUIDS

This invention relates to apparatus for the administration of liquids, and is particularly though not exclusively concerned with apparatus for the gradual and continuous administration of liquids to patients undergoing medical treatment.

It is to be understood that in this specification the term liquid is used to include a mixture of liquids as well as a liquid containing material in solution or suspension or as an emulsion.

The apparatus usually used to administer a liquid to a patient is often referred to as an administration set, and that term will be used in the following description of the invention.

It is sometimes desirable to administer liquids in precisely determined quantities or at precisely determined rates, particularly to children but also to adults when small and critical quantities are concerned. An administration set of a conventional kind for this purpose comprises a piercing cannula adapted to be inserted into a bottle or other liquid container, flexible tubing leading from the piercing cannula, a clamp for controlling the flow of liquid from the container, and a calibrated vessel referred to as a burette and connected to receive liquid through the tubing under the control of the clamp. An outlet from the burette leads to a filter, a drip chamber and a flow-rate regulator and thence to the patient. The burette is provided with a vent which allows air to escape as it fills with liquid and allows air to enter as the liquid flows from it. The vent is protected by an air filter which serves to prevent the liquid in the burette being contaminated by dust particles. The walls of the burette are transparent and carry calibration marks enabling the volume of liquid entering and leaving the burette to be measured.

That type of administration set has several deficiencies. Firstly the air filter can become wetted by the liquid, and this both prevents the air passing through it freely and permits potentially harmful bacteria to enter the burette. Secondly, if the burette is allowed to empty completely, air can enter the tubing downstream of the burette and may accidentally enter the patient with serious consequences. Some types of administration sets have ingenious valves at the outlet of the burette intended to reduce this risk but they are not always satisfactory. The cross-sectional dimensions of the burette are a compromise between being narrow enough for accurate measurement yet not so narrow that the fall in pressure-head as it empties seriously alters the rate of the administration. There are also the usual problems associated with judging the level of the meniscus, particularly when opaque liquids are used such as blood. If use of the burette is no longer necessary, as for example when the critical phase of a patient's illness has passed, the presence of the air vent prevents the set from being used in the simpler mode with the liquid flowing continuously from the bottle through the burette. The burette also tends to make the set bulky and difficult to pack in a sterilizable container.

An aim of the present invention is to provide an improved apparatus enabling at least some of those disadvantages outlined above to be overcome or at least to be reduced.

According to the present invention there is provided apparatus for the administration of a liquid comprising a readily collapsible but substantially inextensible container, a duct through which liquid can leave the container, and take-up means operative to restrict the volume of the operative part of the interior of the container, that is the part communicating with the duct, the take-up means being adjustable so as to vary the volume of the operative part, and calibration means enabling that volume or at least changes in that volume to be determined.

The apparatus would usually be used in the following manner. A quantity of liquid to be administered is introduced into the interior of the operative part of the container, usually by way of the duct but not necessarily so, and the take-up device is so positioned that the operative part of the container, that is the part between the duct and the take-up device, is full, and the volume of liquid in that part of the container can be determined by reference to the calibration means. The liquid can then be gradually withdrawn from the operative part of the container. As the liquid is withdrawn, either the operative part of the container gradually collapses or its volume is continuously reduced by the automatic and continuous adjustment of the take-up means so as to maintain that part full. The operative part of the container can be completely emptied in use, in which case the volume of liquid administered is that initially determined by reference to the calibration means. Normally, however, it is undesirable for the operative part of the container to be completely emptied, and at some appropriate time before it is emptied the volume of liquid remaining in the operative part of the container is determined. If the take-up means has remained in its initial position, it is then moved manually to a position such that the remaining liquid fills the operative part of the container, and the volume of that part is determined by reference to the calibration means. Alternatively the take-up means may have automatically moved to that position in which case the volume is determined without further manual adjustment being necessary. The volume of liquid which has been withdrawn from the operative part of the container is, of course, the difference between the volume first determined and the volume later determined. The calibration means may be such as to enable the volume of liquid in the operative part of the container at any one time to be measured, or alternatively the calibration means may be such that although the total volume in the operative part cannot be measured, changes in that volume from one time to another can be measured. Where the take-up means does not operate continuously and automatically it may be desirable, after the initial volume of liquid has been determined to adjust the take-up means in such a manner as to increase the volume of the operative part of the container, the liquid in that part of the container then no longer filling that part, and that part of the container thus partially collapsing. This technique ensures that the liquid is subjected to no excess pressure due to any innate resilience in the material from which the container is made or due to any tendency for the take-up means to reduce slightly the volume of the operative part.

Although a container is usually provided with a single duct it is within the scope of the invention to provide more than one duct communicating with the interior of the operative part of the container.

The calibration means preferably comprises calibration marks on the container which co-operate with an index, such as an edge or cursor, on the take-up means.

The take-up means may comprise external bearing members, such as jaws or rollers which cooperate to trap the container between them and, by pressing the opposite walls of the container together, to close the interior of the container at that place. Alternatively the take-up means comprises a device for rolling up the container from one end. In another alternative the take-up means comprises a piston or like plunger which is movable inside the container.

The liquid may leave the container under the effect of gravity, or alternatively or in addition displacing means may be provided tending to compress and to reduce the volume of the operative part of the container. The displacing means may continuously urge the take-up means in such a direction as to tend to reduce the volume of the operative part of the container, or alternatively the displacing means may be independent of the take-up means and for example comprise a pair of plates, one on each side of the operative part of the container, urged together by spring means or by gravity.

The container would usually be made of a transparent material, but this is not essential, and it may be opaque.

An embodiment of the invention will now be more particularly described, by way of example, with reference to the accompanying drawings, in which:

FIG. 1 is a perspective view of an administration set in accordance with the present invention, the outlet end being omitted, FIG. 2 is a plan view of a component of the administration set shown in FIG. 1, the component being opened out so that its construction can be more readily seen, FIG. 3 is a side view of the component shown in FIG. 2, FIG. 4 is a perspective view, to a much larger scale, of another component of the set shown in FIG. 1, parts being broken away to reveal other parts thereof, FIG. 5 shows a short length of the tubing incorporated in the administration set shown in FIG. 1, and FIG. 6 is a side view of the outlet end of the administration set shown in FIG. 1.

The administration set shown in FIG. 1 is intended for use in administering a liquid to a patient undergoing medical treatment. The set would normally be provided for use in a sterile condition, and would be discarded after use. Most of the component parts of the set are made from plastics materials.

The set has a piercing cannula 1 of conventional form fitted to one end of a short length of flexible tube 2. The tube 2 is transparent and is made of polyvinylchloride. The tube 2 extends through a clamp 3 of known type comprising a metal plate with a tapered slot 4 which is wider at one end than the other. In the position shown, with the tube 2 at the wider end of the slot 4, an unobstructed flow of liquid through the tube can occur. When the plate is displaced so that the tube approaches the narrower end of the slot the tube is squashed so that no liquid can flow through it.

The tube 2 leads to one end of a Y-shaped connector 5. One of the other branches leads to a tube 6 which is connected to a container 7 of the kind characteristic of the present invention, while the other branch leads to the outlet end of the set by way of a filter 8, an adjustable regulator 9 and a flow-measuring device 10. The filter 8 is of conventional construction, comprising a sealed container with a bag inside it made of a woven fabric, the interior of the bag leading to the outlet of the container.

The regulator 9 is a form of the means for controlling fluid flow which is the subject of my U.K. patent application No. 1,361,405 (equivalent to U.S. Pat. No. 3,779,507). Briefly the regulator comprises a length of flattened tube 11, of which the abutting inner faces are formed with aligned tapered grooves 12. An adjustable clamp 13 holds the walls of the tube together at any selected point along the tube 11. Upstream and downstream of the clamp the resilience of the walls of the tube 11 causes it to open out, but where the clamp holds the tube closed the liquid is constrained to flow through the grooves 12. The rate of flow depends on the size of those parts of the grooves held together by the clamp. The construction of the clamp differs from that illustrated in the aforementioned patent application. The clamp 13, shown in detail in FIG. 4, comprises two identical plastics mouldings each with a bearing plate 14 and a finger plate 15 held in spaced parallel relationship by an integral spacer 16. The sides of the bearing plates 14 are notched near their ends, and rubber bands 17 are located in the notches and serve to urge the bearing plates 14 together. If the finger plates 15 are gripped between the fingers the bearing plates can be moved apart from one another against the action of the rubber bands 17. A portion 18 of the tube 11 has no grooves 12. When the clamp is placed there the liquid cannot flow. When the clamp is placed in any position and the finger plates are gripped adjacent to one of the spacers 16 and not adjacent to the other, the mouldings tilt. The edges of the bearing plates 14 still grip the tube 11 sufficiently to prevent the clamp sliding along the tube out of position, but the walls of the tube can part to allow the liquid to flow rapidly through the tube. This is useful when it is necessary temporarily to increase the flow but it is also necessary to restore later the previous slow rate of flow.

The flow-measuring device 10 is the subject of my U.K. patent application No. 18518/71 (equivalent to U.S. application Ser. No. 258,370). It does not form a direct part of the present invention and therefore it will not be further described here.

The container 7 is made from two long rectangular sheets of flexible but substantially inextensible plastics film placed one over the other and welded together along the edges. One end of the tube 6 is sealed between the sheets of film, at one end of the container, so that fluid can pass through the tube into the container. A transverse weld 19 is made some distance from the opposite end of the container so as to leave a tab 20.

A take-up device 21 is mounted on the container 7 and comprises a pair of identical frames 22 connected by a flexible hinge strip 23. The frames illustrated are made from metal, but in an alternative construction (not illustrated) they are made as a unitary moulding, from a plastics material such as polypropylene, with an integral hinge. Each frame 22 is approximately square. That side of each frame parallel with the hinge but spaced from it is shaped to present a part-cylindrical bearing surface 24. The sides of each frame between the bearing surface 24 and the hinge 23 have flanges 25 normal to the main plane of the frame. Adjacent to the bearing surface 24 each flange 25 is formed with a pair of notches 26 which define between them a lug 27. As shown in FIG. 1, when the take-up device is assembled for use the frames 22 are held together by rubber bands 28 passing round the lugs 27. Locating pegs 29 by the hinge 23 enter complementary holes 30 when the frames are assembled face to face, and locating lugs 31 at the ends of the bearing surfaces 24 likewise enter complementary slots 32. Thus in use the frames 22 cannot twist or slide relatively to each other.

The container 7 extends between the bearing surfaces 24 of the take-up device 21 and thence through the central opening in one of the frames. The forces exerted by the rubber bands 28 are such that liquid cannot leak from the operative part of the container, that is the part between the tube 6 and the take-up device 21, into the remaining part of the container, that is the part between the take-up device and the tab 20.

The container 7 carries calibration marks 33 which co-operate with the hinge end 34 of the take-up device, which thus constitutes an index.

When the operative part of the container 7 is full of liquid, that is it contains the maximum quantity of liquid which it can accommodate, the operative part of the container is distended and becomes approximately cylindrical in shape. As the sides of the container are mutually parallel the calibration is linear over almost all of its extent, the calibration being non-linear only in respect of that portion of the container close to the tube 6.

The administration set is used in the following manner. It is packed with just the tab 20 of the container 7 drawn into the take-up device and is folded to fit into the porous envelope in which it is sterilized. The set is removed from the envelope and the regulator 9 closed. The piercing cannula 1 is forced into the appropriate opening of a bottle containing the liquid to be administered, breaking its seal, and the bottle is suspended, cannula downwards, from the hook of a suitable stand. The liquid flows into the depending container 7 and filter 8, trapping some air in each. This air is displaced into the bottle by squeezing the container 7 and the filter 8 several times. Alternatively the take-up device 21 may be slid to the inlet end of the container 7 before the cannula 1 is inserted into the bottle. The take-up device can then be slid back, thus allowing the container to fill with liquid. After the air has been expelled an airway of conventional form is inserted into the bottle. The clamp 13 is then opened widely for a short period to fill the rest of the set and flush out the rest of the air trapped in the tubing. The clamp 3 is closed, so isolating the bottle, and the device 21 is hung from the hook on the stand. The terminal connector is connected to the tube leading into the patient and the flow of liquid is determined by adjusting the regulator 9 and counting the rate of passage of drops through the flow-measuring device 10. At intervals during the day the amount of liquid that has entered the patient is measured by unhooking and lowering the take-up device 21, pulling the container 7 through it by means of the tab 20 until further movement is resisted by the incompressible column of liquid in the now tense operative part of the container and then noting the calibration mark that is in line with the straight index edge 34 of the device 21. After replacing the take-up device on the hook the tension in the container is released by pulling the container down about one centimetre. When empty the container is refilled by pulling it the whole distance back through the take-up device 21, allowing it to hang down on the tube 6 and opening the clamp 3. If a definite volume of liquid which is less than that held by the full container is to be administered the take-up device is set to the appropriate calibration mark before the container is allowed to fill.

When a change in the type of liquid is prescribed the liquid already in the container can be emptied back into the bottle by opening the clamp 3 and gently pulling the container the full distance through the take-up device by means of the tab 20. Most of the contents of the filter 8 may be similarly emptied by squeezing it, with the clamp 3 open, provided its walls are sufficiently flexible; care is then taken to close the clamp 3 before changing the bottle. The majority of administration sets have a latex rubber injection site (see FIG. 6) near the terminal connector and, if the tubing between that site and the connector can be clamped, an even more complete change of the liquid in the set may be achieved by inserting a sterile hollow needle through the injection site. This allows the first liquid to escape while the new liquid flows from the bottle into the upper part of the set.

The administration set described above with reference to FIGS. 1 to 4 has many advantages over previously existing sets. As the burette or container 7 has no air vent there are none of the problems previously described concerning the air-filter and the risk of air becoming infused into the patient. The set is easier to prepare since the filling of the container requires no attention and it also does not need to be refilled after the set has been flushed through. The pressure-head generated by the liquid in the container is about half as great again as that with the conventional burette (an important advantage when the infusion is being made through a fine needle) and it is maintained virtually constant as the container empties. The method of reading the volume of liquid administered is precise because a relatively narrow container is used and there are no problems associated with a meniscus. The container can in effect be removed from the system if it is not needed. As the container can be emptied back into the bottle a more rapid change can be made in the type of liquid being infused than was previously possible. Since the container packs flat the whole set may be placed into a sterilizable envelope and subsequently used in a sterile area; the bulkier conventional set is usually packed in an unsealed box and its outside surfaces do not remain sterile.

When only small volumes of liquid are needed an alternative arrangement is for the liquid to be dispensed in the container, which is then provided with a take-up device. An excess volume of liquid is dispensed for filling and flushing out the set. The tube 2, connector 5 and clamp 3 are not required. Air trapped in the filter 8 is transferred to the operative part of the container and then squeezed passed the take-up device 21 into the remainder of the container, together with any excess fluid.

There are many circumstances where although a liquid needs to be administered slowly, and in a certain dose, the exact rate of administration is not critical. In such a circumstance a simplified method could be employed with the container alone connected directly to the patient either through an adjustable regulator, the resistance of which was roughly calibrated, or through one of a series of interchangeable fixed resistance units. Protection from overdosage could be gained by having only the immediately required dose in the operative part of the container. If necessary the usual gravity feed, with its long tubing and awkward stand, could be avoided by placing the container between two plates pressed together by a spring mechanism or simply by a weight. For small volumes of liquid the whole apparatus could be made small enough to be attached to the patient and so permit him to be ambulant.

One of the problems which arises with administration sets whether of the conventional kind or the kind described above, is that the lengths of tubing, such as the tubing 6 and that leading from the flow-measuring device 10 to the terminal connector, tend to kink and thus prevent the flow of liquid through them.

I have now found that this tendency can be reduced by using tubing of oval or like cross-section. A typical section of the preferred tubing is shown at 35 in FIG. 5. In one method of manufacture soft polyvinylchloride tube of circular cross-section is made by a conventional extrusion process and while still hot is passed between spaced rollers. In an alternative method the tube is extruded through a die of oval or other appropriate shape.

In use the tubing tends to bend about axes parallel with the maximum cross-sectional dimension of the tubing, but although its internal cross-section is thereby reduced to some extent the flow of liquid is scarcely affected, and the tendency to kink is very greatly reduced.

In spite of its non-circular cross-section it is found that the ends of the tubing can readily be joined to rigid connecting tubes of circular cross-section, the tubing being easily distorted to a circular cross-section.

As indicated above this form of tubing may be incorporated in administration sets of any type.

The administration sets embodying the invention, and other types of administration sets as well, require some form of preparation before use, and it is usually better for this preparation to be done before the patient is prepared. Where the bacteriological barrier provided by the cover for the terminal connector has to be broken in order to flush air out of the system some means of reforming it is desirable to prevent the connector from becoming contaminated, particularly if there is some delay due to difficulties with inserting the needle, cannula or catheter into the patient. A simple form of cover for this purpose is illustrated in FIG. 6 and consists of a short length of flexible tubing 40 of circular cross-section, similar to that used in the conventional administration sets. One end of the tubing 40 is pushed over the terminal connector 41, while the other end has an air-filter, such as a cotton wool plug 42. This cover is kept in place while air is flushed out of the set, though it is important that there is no back-flow. Then the tubing 40 is firmly occluded in its middle region by a clamp or by folding it over to produce a severe kink which is then kept sealed by pressing a piece of flexible tube 43 of somewhat wider bore over the folded portion. This folded portion also makes a useful hook with which to suspend the terminal connector 41 and so prevent it from accidentally falling to the dust-contaminated floor. The set is thus completely protected and may be safely left for several hours if necessary. When the needle, cannula or catheter has been satisfactorily inserted into the patient this cover tubing 40 is pulled off the terminal connector 41 and the connection made. The terminal connector 41 is joined to the remainder of the set by tube 44 which may be of oval or like cross-section if desired.

FIG. 6 also shows at 45 the injection site, referred to earlier, near the terminal connector 41.

Again, this cover may be used with administration sets of any type.

I claim:

1. Apparatus for the administration of a liquid comprising a readily collapsible but substantially inextensible container, duct means adapted to be connected to a source of liquid and through which liquid enters and leaves the container, and take-up means operative positively to restrict the volume of the operative part of the interior of the container, that is the part communicating with the duct, so that the remainder of the interior of the container is inaccessible from the operative part thereof, the take-up means being infinitely adjustable so as to vary the volume of the operative part between limits, and calibration means enabling that volume or at least changes in that volume to be determined.

2. Apparatus according to claim 1 in which the container is of elongated tubular form, with the duct means entering its operative part at one end.

3. Apparatus according to claim 1 in which the calibration means comprises calibration marks on the container which co-operate with an index on the take-up means.

4. Apparatus according to claim 1 in which the take-up means is manually adjustable to enable the volume of the operative part of the container to be varied intermittently and at will.

5. Apparatus according to claim 1 in which the take-up device comprises external bearing members operative to trap the container between them and, by pressing the opposite walls of the container together, to close the interior of the container at that place.

6. Apparatus according to claim 1 in which the duct leads to a junction in an enclosed liquid path extending between a liquid inlet and a liquid outlet.

7. Apparatus according to claim 6 in which the liquid inlet comprises a piercing cannula, and in which there is means operative to prevent the flow of liquid through the enclosed liquid path between the liquid inlet and the junction.

8. Apparatus according to claim 6 in which the liquid path between the junction and the liquid outlet includes a filter.

9. Apparatus according to claim 6 in which the liquid path between the junction and the liquid outlet includes a flow regulator operative to control the rate of flow of liquid through it.

10. Apparatus according to claim 6 in which the liquid path between the junction and the liquid outlet includes a flow-measuring device operative to enable the rate of flow of the liquid through it to be measured.

11. Apparatus according to claim 1 in which at least the duct comprises flexible tube of oval or like cross-section.

12. Apparatus according to claim 1 in which the duct is connected to a terminal connector provided with a removable cover comprising a length of flexible tube with a filter at its free end, and a hollow component adapted to receive a kinked portion of that tube so as to maintain that portion in its kinked state, the tube being occluded at the kink.

* * * * *